(12) United States Patent
Eden

(10) Patent No.: US 7,623,242 B2
(45) Date of Patent: Nov. 24, 2009

(54) DEVICE AND METHOD FOR MONITORING MULTIPLE CHEMICAL SAMPLES WITH A FLUORESCENT TUBE

(76) Inventor: Gideon Eden, 2765 Ember Way, Ann Arbor, MI (US) 48104

( * ) Notice: Subject to any disclaimer, the term of this patent is extended or adjusted under 35 U.S.C. 154(b) by 155 days.

(21) Appl. No.: 11/766,196

(22) Filed: Jun. 21, 2007

(65) Prior Publication Data

US 2008/0316467 A1   Dec. 25, 2008

(51) Int. Cl.
*G01N 21/25* (2006.01)
(52) U.S. Cl. ..................................... 356/417
(58) Field of Classification Search .................. 356/51, 356/73, 317, 417
See application file for complete search history.

(56) References Cited

U.S. PATENT DOCUMENTS 6,577,393 B1 *   6/2003   Potzschke et al. ........... 356/364

2007/0121111 A1 *   5/2007   Blumenfeld et al. ........ 356/318

* cited by examiner

*Primary Examiner*—Michael A Lyons
*Assistant Examiner*—Abdullahi Nur
(74) *Attorney, Agent, or Firm*—Young Basile

(57) ABSTRACT

A monitoring device is described for multiple chemical reactions in multiple test containers. Each container contains chemical reagents and at least one fluorescence dye indicator capable of changing its fluorescent characteristics due to the chemical reaction. A single cylindrical ultraviolet (UV) cold cathode fluorescent (CCFL) tube is utilized. Multiple test containers (e.g., 8) are placed along the tube of the CCFL. The UV light emerging from the CCFL interacts with the dye indicator in each of the containers to yield interactive light beams that can be detected by signal photo sensors. In order to compensate for the light variations occurring along the tube, a reference photo sensor is placed for each container location along the tube to directly detect the signal from the CCFL. By normalizing the signal generated by the signal photo sensor to the signal of the corresponding reference photo sensor, the value of the normalized signal is independent of any light source variations along the tube due to CCFL aging and repetitious power switching. Consequently, the normalized signals only correspond to chemical variations occurring in the test containers.

11 Claims, 1 Drawing Sheet

DEVICE AND METHOD FOR MONITORING MULTIPLE CHEMICAL SAMPLES WITH A FLUORESCENT TUBE

BACKGROUND AND PRIOR ART

In many scientific disciplines, it is desirable to monitor the chemical reactions of a multiplicity of test samples. Such reactions can occur within specific time durations from a few seconds to days or weeks. One convenient and economical methodology is optical monitoring that can be applied if the chemical reactions modify certain optical characteristics of the test samples. For example, fermentation reactions can change the pH of a liquefied sample. If a pH color indicator is used, its color change can be detected by optical means as a function of time.

Many chemical reactions are associated with modification of the fluorescence characteristics of the test sample. Many fluorescence dyes have been developed for various chemical reactions. For example, Rhodamine-based compounds fluoresce when exposed to visible light radiation. Other compounds, such as Coumarines, fluoresce when exposed to long ultraviolet (UV) radiation. The advantage of the fluorescence compounds is that they are very sensitive and can provide early indication of specific occurring reactions.

The popularity of fluorescence monitoring has resulted in the introduction of special instruments which are based on fluorescence essays. Quite a few commercial instruments are available, based upon the following principles:

1. Single source single detector: This type is the traditional and most sensitive configuration. It usually utilizes a strong UV light source covering short UV bands, long UV bands and short visible bands (violet and blue). A UV filter to restrict the radiation to a specific UV wavelength is used. A single sensitive detector, such as a photo multiplying tube (PMT), combined with a visible light filter is utilized to detect the visible fluorescence light generated from the test sample due to the optical interaction of the sample with the light generated by the UV source. While this configuration is widely used due to its sensitivity, it has two major deficiencies. First, the light source, which is typically a strong discharge lamp, has a short life span—several hundreds hours—and has to be replaced often. Consequently, its price and maintenance prohibit its use for large scale automated processes, and therefore its usage is limited to few laboratory tests.
2. Indexed: To apply the above single source single detector configuration to multiple systems, a mechanical indexing means is utilized. Typically a micro-titer plate with multiple wells is indexed between the energy source and the detector (Bioscan Chamelton Multilabel Plate Reader). In modern systems, the UV light is conveyed from the light source via fiber optic cable. The emitted light can also be conveyed via another fiber optic line to the detector. With this configuration, multiple samples can be monitored, but the indexing means complicates the system and shortens its average failure time. The light source is still expensive, requiring frequent replacements.
3. Ultraviolet light emitting diode (UV LED): With the introduction of UV LED, some commercial systems (Turner BioSystems TBS-380) are available. Typically, a photo diode or PMT is used to detect the visible fluorescing light. With this configuration, multiple LEDs and photo detectors can be used for multiple tests. The main disadvantage of this configuration is the wavelength of the UV LED, which borders the visible light range (380-400 nanometers). For many reactions, this wavelength is not sufficiently short, yielding low fluorescence output.

SUMMARY OF THE INVENTION

The main goal of the present invention is to provide a simple device to monitor test samples with the following features:
Simultaneous multiple samples monitoring
Excitation of ultraviolet energy at or below 360 nanometers
Long life of the ultraviolet source (~10,000 hours of continuous use)
No mechanical or moving parts The main principle of this invention is to employ an elongated cold cathode fluorescence tube (CCFL) as an ultraviolet light source. This gas discharge tube is capable of generating short UV radiation due to the spectral components of its gas. If the tube is coated with fluorescing material, long UV radiation (~360 nanometers) is emitted from its surface. This radiation, also known as black light, can excite many fluorescence dyes to generate visible light. Unlike other high power UV discharge lamps that are high power wide spectrum but have a lifetime of few hundred hours, CCFLs can easily last for tens of thousands of hours of continuous operation. In addition, the elongated shape makes it possible to locate multiple test samples along the CCFL tube.

BRIEF DESCRIPTION OF THE PREFERRED EMBODIMENT FIGURES

DESCRIPTION OF THE PREFERRED EMBODIMENT

Figure 1:
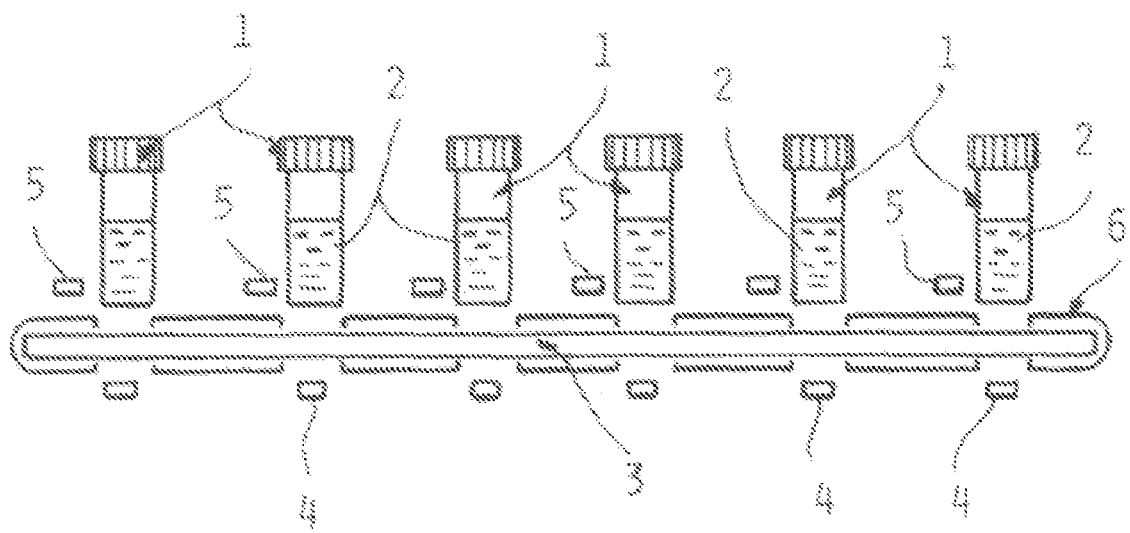
FIG. 1 is a diagrammatic view of a preferred embodiment of a testing device for testing multiple test samples.
Figure 2:
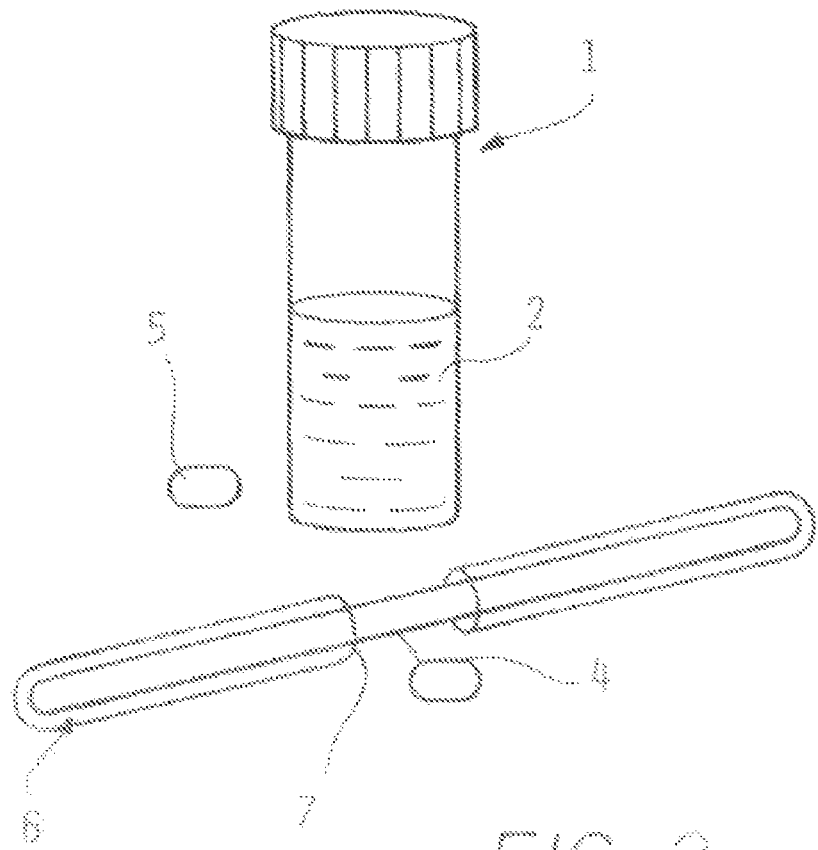
FIG. 2 is an enlarged diagrammatic view of a testing device for testing a single test sample.

A general configuration of the invention is illustrated in FIGS. 1 and 2. Each test sample is inserted into a test container 1 containing mixture 2 of the chemical assay and at least one dye indicator capable of changing its fluorescent characteristics due to the occurring chemical reaction. A single cylindrical ultraviolet light source, consisting of a cold cathode fluorescent tube 3, is utilized instead of multiple light sources. The tube 3 can be inserted into a protective sleeve 6 that has discrete openings 7 that allow UV light to radiate the test sample. The multiple test containers are placed in front of these openings. The light emerging from each opening interacts with the dye indicator substrates in the container to yield an interactive light beam that can be detected by a photo sensor 5. The protective sleeve can be made of metal in order to shield electrical noise generated by the tube 3. In this configuration, a CCFL, such as BF3221 (JKL Components Co., Pacoima Calif. USA), is 21 cm long. If every test container has a 2 cm diameter, then 8-10 test containers can be excited with a single tube.

In order to compensate for any light variations occurring along the tube, a reference photo sensor 4 is located next to each test container. This photo sensor 4 is placed as close as possible to the source origin or discrete opening 7 along the tube. The photo sensor 4 can be placed at a reference point located 90° along the circumference of the cross section of the cylinder at the discrete opening 7. If for any reason the local intensity of the light changes at a specific container location, the corresponding photo sensor 4 can measure this change. By normalizing the signal generated by the photo detector 5 to the signal of the reference photo sensor 4 using a normalization algorithm, the value of the normalized signal is independent of any local light variations, and thereby reflects only chemical variations occurring in the test container. The photo sensors 4 and 5 can be wide band detectors, such as photo-diodes or photo-transistors. The photo sensor 5, measuring the interaction visible light can be restricted to a specific spectrum range with an additional band-pass optical filter.

The invention claimed is:

1. A device for analyzing multiple chemical samples, comprising: an elongated light source;
    a plurality of Locators, each Locator positioning an associated chemical sample in a specific location along said elongated light source to enable separate emerging light beams emitted from multiple points along said elongated light source to impinge each of the respective chemical samples;
    multiple light detectors each positioned relative to each of said multiple chemical samples to detect interactive light beams generated from each chemical sample, resulting from the optical interaction of each of said emerging light beams with the corresponding chemical sample: and a reference detector reading the intensity of said light source and consequently determining the relative intensity of each of said emerging light beams.

2. The device of claim 1 wherein said reference detector comprises multiple reference sensors each placed at a predetermined distance from a corresponding emerging light beam, located along a circumference of the cross section of the elongated light source at each of said emerging light source.

3. The device of claim 1 wherein said elongated light source comprises a gas discharge lamp.

4. The device of claim 3 wherein said gas discharge lamp emits visible light.

5. The device of claim 3 wherein said gas discharge lamp emits ultraviolet light.

6. The device of claim 1 wherein each of the chemical samples is contained in a light. transparent container.

7. A method of analyzing multiple samples utilizing the device of claim 1, comprising the steps of:
    placing the chemical samples along said elongated light source with the aid of said locator means;
    switching on said elongated light source;
    measuring the individual signals generated by said light detectors; and
    analyzing each of said signals to determine a measurable chemical property of the corresponding chemical sample.

8. The method of analyzing multiple chemical samples, according to claim 7 further including comprising:
    repeating the steps in claim 7 at predetermined time intervals to obtain time sequence data from said signals; and
    analyzing the pattern of said time sequence data to determine chemical changes taking place in said samples at said time intervals.

9. The method of analyzing multiple samples according to claim 2, comprising the steps of:
    placing the chemical samples axially along said elongated light source with the aid of said locator;
    switching on said elongated light source;
    measuring the individual signals generated by each of said light detectors, and the corresponding reference signals;
    applying a normalization algorithm based upon each of said individual and each of said reference signals, to obtain normalized signals which are independent of variation of the light intensity generated from each of said emerging light sources; and
    analyzing said normalized signals to determine a measurable chemical property of the corresponding chemical samples.

10. The method of claim 9 wherein said normalization algorithm is the ration of said assay signal with said reference signal.

11. The method of analyzing multiple chemical samples, according to claim 9 including:
    repeating the steps in claim 9 at predetermined time intervals to obtain time sequence data from said normalized signal; and
    analyzing the pattern of said time sequence data to determine chemical changes taking place in said samples at said time intervals.

* * * * *